United States Patent [19]

Espitalie et al.

[11] 4,153,415
[45] May 8, 1979

[54] METHOD FOR DETERMINING OIL-RELATED CHARACTERISTICS OF GEOLOGICAL SEDIMENTS FROM SMALL SAMPLES THEREOF

[75] Inventors: Jean Espitalie, Le Vesinet; Jean-Loup Laporte, Rueil-Malmaison; Marcel Madec, Suresnes; François Marquis, Saint-Prix, all of France

[73] Assignee: Institut Francais du Petrole, France

[21] Appl. No.: 760,524

[22] Filed: Jan. 19, 1977

[30] Foreign Application Priority Data

Jan. 20, 1976 [FR] France .............................. 76 01765
Nov. 12, 1976 [FR] France .............................. 76 34402

[51] Int. Cl.² ............................................ G01N 31/12
[52] U.S. Cl. ............................ 23/230 EP; 23/230 PC; 422/80
[58] Field of Search ....... 23/230 PC, 253 PC, 230 EP

[56] References Cited

U.S. PATENT DOCUMENTS

| | | | |
|---|---|---|---|
| 2,686,211 | 8/1954 | Cargill | 23/253 PC X |
| 3,033,287 | 5/1962 | Bond | 23/230 EP X |
| 3,049,409 | 8/1962 | Dower | 23/230 EP |
| 3,703,355 | 11/1972 | Takahashi et al. | 23/230 PC |
| 3,898,041 | 8/1975 | Stephens et al. | 23/230 PC |
| 3,953,171 | 4/1976 | Espitalie et al. | 23/253 PC X |

*Primary Examiner*—Joseph Scovronek
*Assistant Examiner*—Arnold Turk
*Attorney, Agent, or Firm*—Craig & Antonelli

[57] ABSTRACT

The method comprises heating a sample successively to a first temperature comprised in the range from between 200° to 400° C., then to a second temperature preferably from 550° C. to 600° C., measuring the amount of native hydrocarbons vaporized at the first temperature and the amount of hydrocarbon compounds produced by pyrolysis of the organic material of the sample at the second temperature.

Characteristics of the sediments are derived from the two measured values.

10 Claims, 9 Drawing Figures

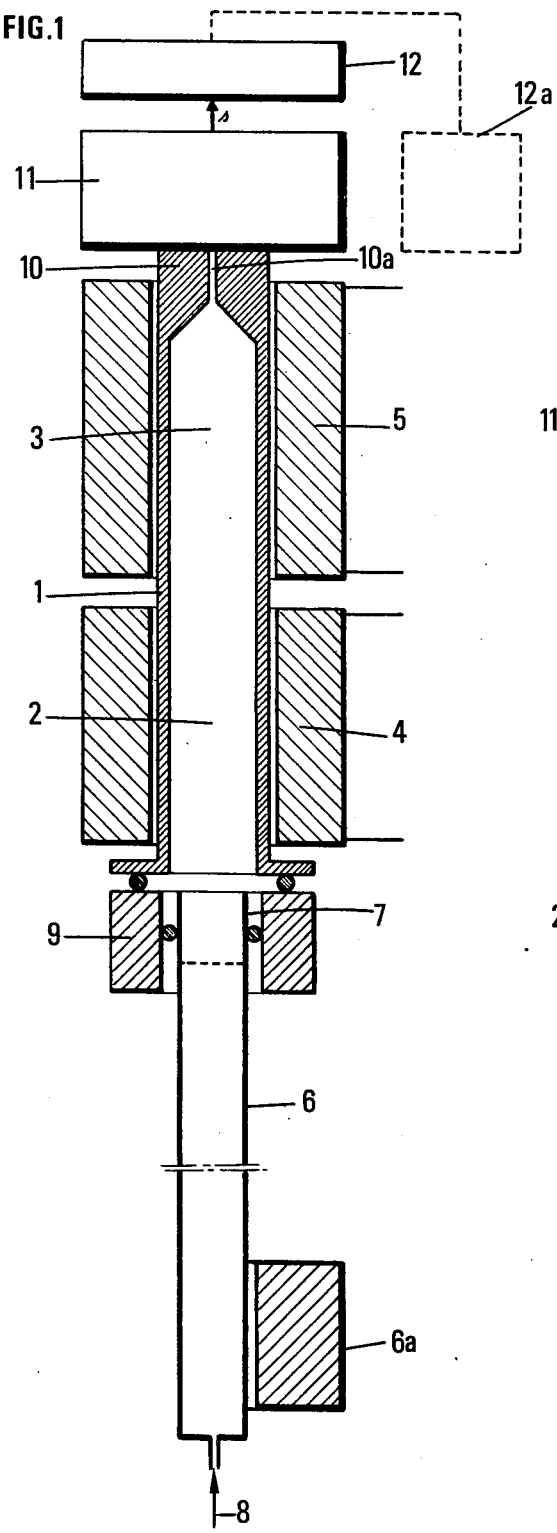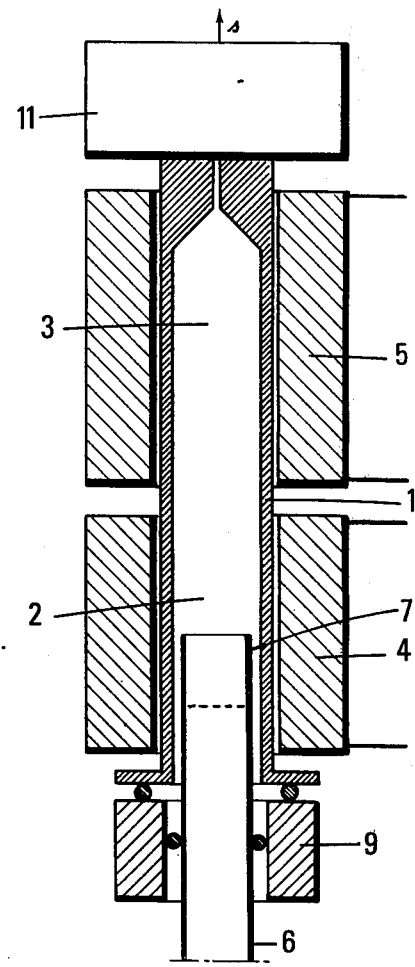

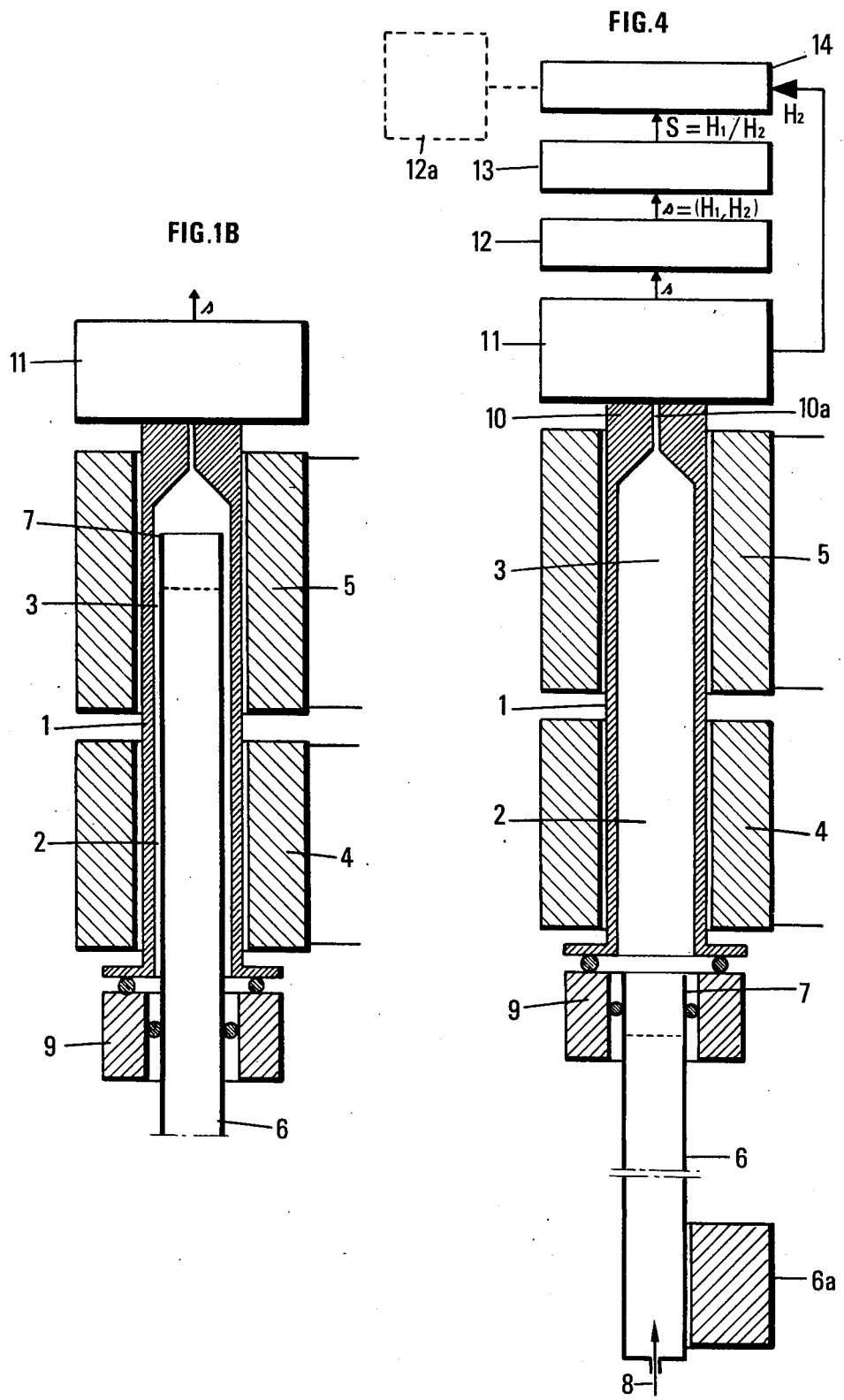

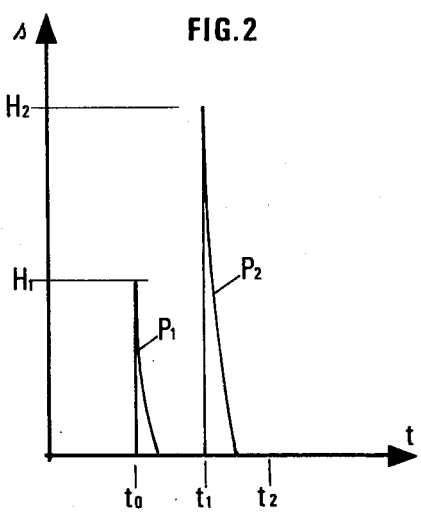
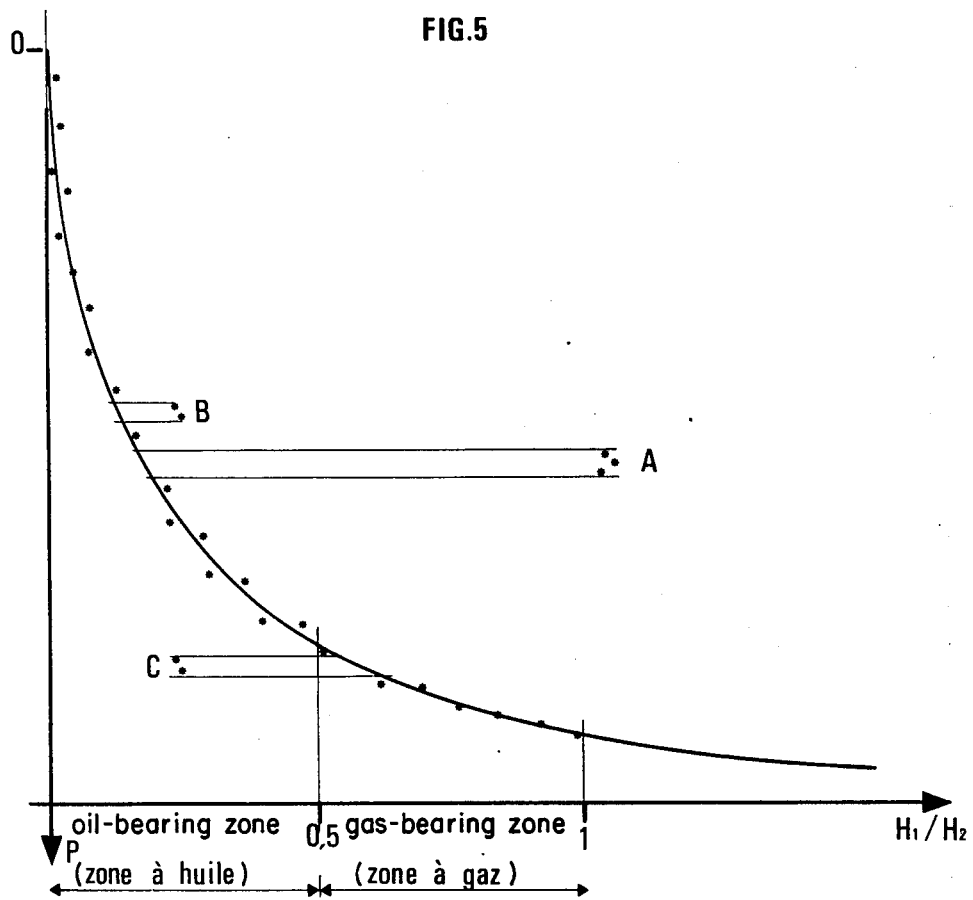

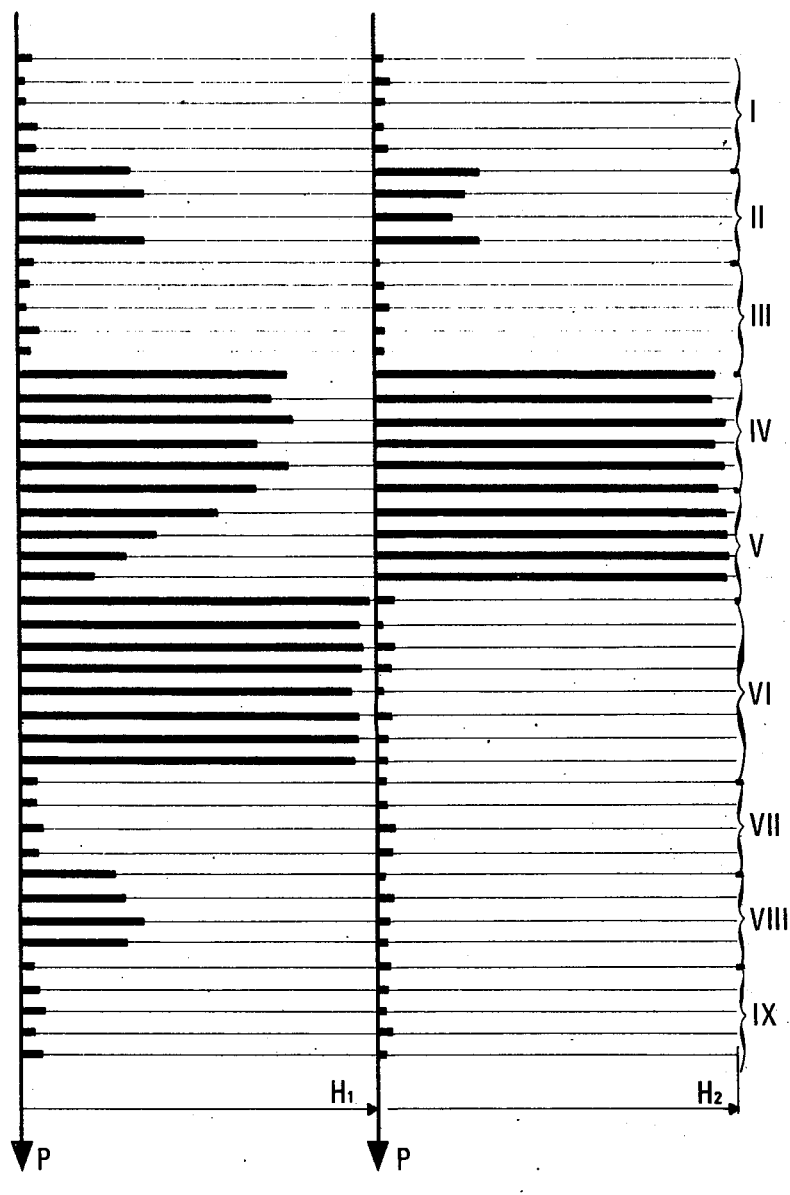

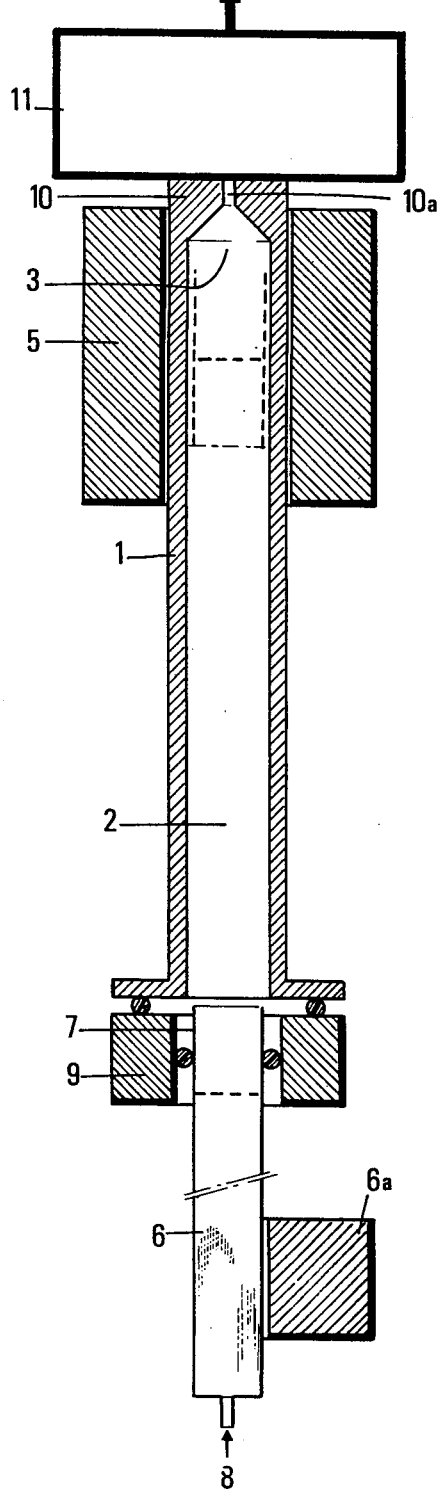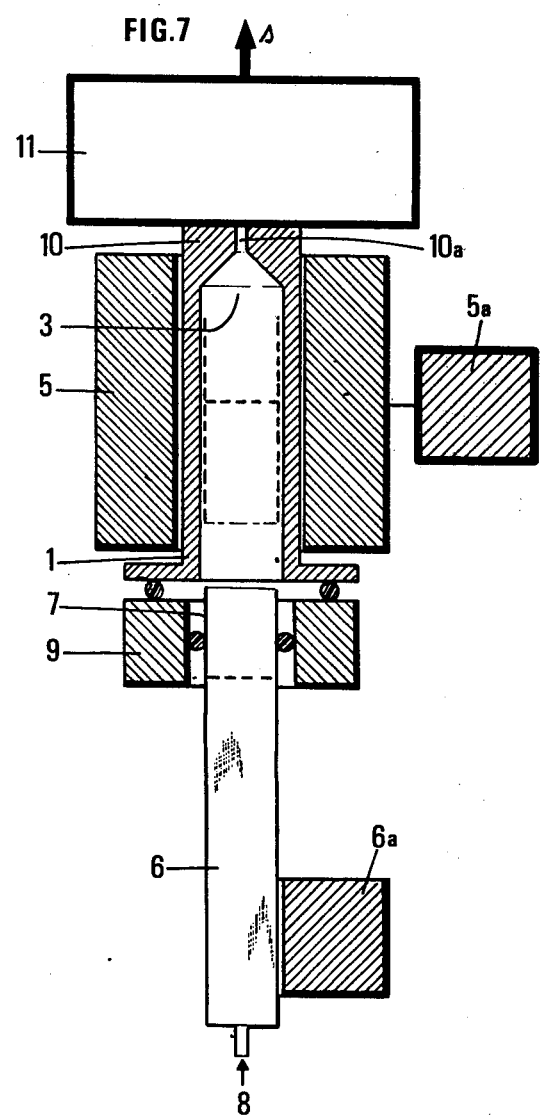

METHOD FOR DETERMINING OIL-RELATED CHARACTERISTICS OF GEOLOGICAL SEDIMENTS FROM SMALL SAMPLES THEREOF

The present invention relates to a method of/and an apparatus for determining at least some of the oil-related characteristics of geological sediments, such as, for example, but not exclusively, the capacity of the sediments to produce oil, either right now or in the future, i.e. the capacity of these sediments to constitute a good mother or source rock for hydrocarbons or to be a reservoir rock for hydrocarbons.

Let be recalled some well known principles, for a better understanding of the following description:

hydrocarbon compounds, mainly those which can be extracted by organic solvents, originate from insoluble organic material-or kergen- under the action of the pressure increase which results from the burying of the sediments in a sedimentary basin;

the determination of the respective quantities of soluble organic material (hydrocarbons), on the one hand, and of insoluble organic material, on the other hand, contained in the sediments is of great interest in oil exploration, since it has been shown that:

(a) the quantity of hydrocarbons formed in the sediments increases regularly with increasing burying depth of these sediments It is thus possible to evaluate the degree of evolution of the organic material contained in these sediments and more particularly the interval of this evolution which corresponds to the main phase of oil formation;

(b) these native hydrocarbons are those which under some conditions, will be released from the source rock wherein they were formed, and will constitute oil accumulation in the reservoir rocks;

(c) the nature of the insoluble organic material contained in the rocks determines the oil production capacity of these rocks, i.e. their lesser or greater capacity to produce oil compounds.

It appears then that a systematic analysis of these organic compounds will make it possible to distinguish among the geological sediments, those which are of the greatest interest for the geologist i.e.:

geological sediments which have released oil (source rocks), sediments which, on the contrary, have stored this oil (reservoir rocks).

The knowledge of such data would enable the drillers to carry out only wittingly, coring operations or reservoir testing operations, which are time consuming and expensive, especially if those informations are obtainable as drilling proceeds.

Although some types of analyses (fluorescence for determining the oil indexes, degassing of the drill cuttings), can already be performed directly on the drilling field, the obtained results are incomplete and not very accurate, thus neither providing all the desired results, nor giving these informations systematically as the cuttings rise to the ground surface.

As regards conventional or laboratory measurements concerning analysis of these different organic compounds, these are time consuming and too expensive technics to be carried out in real time during drilling operations.

The invention provides a method and an apparatus for obtaining very rapidly (within about 4 minutes) informations concerning the oil characteristics of geological formations, on the basis of samples whose weight does not exceed 100 mg and which, when they are collected from drill cuttings, do not require any other preliminary treatment than a simple washing to eliminate the drill mud.

The invention will be properly understood and other advantages thereof will be made apparent from the following description of a non-limitative embodiment, illustrated by the accompanying drawings wherein:

FIG. 1 diagrammatically illustrates a first embodiment of the device according to the invention, FIGS. 1A and 1B show the operation of this device, FIG. 2 shows the general shape of signal S, FIG. 3 is a particular example of application and interpretation of the measurements carried out on drill cuttings, FIG. 4 is an alternative embodiment of the apparatus, FIG. 5 is a particular example of application of the apparatus according to the invention, and FIGS. 6 and 7 illustrate simplified embodiments of the invention.

The method according to the invention for rapidly and accurately evaluating at least one oil-related characteristic of geological sediments, from small samples thereof, comprises the successive following steps;

(a) subjecting a small sample of a geological formation to a first temperature capable of vaporizing all the native hydrocarbons originally contained in the sample without pyrolyzing the organic material of this sample, this temperature being at most 400° C. and preferably from 200° C. to 400° C., (b) measuring the amount of the released hydrocarbons, (c) subjecting the sample to a second temperature for pyrolyzing all the insoluble organic material contained in the sample, this second temperature being from 400° C. to 700° C. and preferably from 550° C. to 600° C., (d) measuring the amount of hydrocarbon products resulting from such pyrolysis, and (e) deducing from these measurements at least one oil-related characteristic of the rock from which the analyzed sample originates.

According to a first alternative embodiment, this oil-related characteristic of the rock is directly derived from the values of the performed measurements.

According to a second alternative embodiment, this oil-related characteristic is derived from a function of the ratio of the two above-defined measurements and of at least one additional parameter, which may be one of said two measured values.

According to a third embodiment of the invention applied to the study of drill cuttings, the oil-related characteristic for the different ground layers traversed by a borehole is derived from the value of the ratio of the measured values and from the variations of this ratio versus the depth at which the cuttings are collected.

The invention may be used for example, but not limitatively, for determining the hydrocarbon production capacity of the rock from which the analyzed sample originates, the oil production capacity of this rock, i.e its capacity to release hydrocarbons, but it will also be possible to determine if the rock is, as called in the art, a hydrocarbon containing reservoir rock, etc.

An embodiment of apparatus for carrying out the method according to the invention is diagrammatically illustrated in FIG. 1. This apparatus comprises a tube or housing 1 which can be heated. This tube is preferably substantially vertical. In the embodiment illustrated by FIG. 1 the apparatus comprises means 4 for heating the lower part 2 of tube 1 and means 5 for heating the upper part of tube 1.

These heating means may be of conventional type and will surround the tube. Alternatively the tube 1 can be made of two electrically conducting parts separated by an insulating portion, heating being achieved by electric current flowing through the two conducting parts of tube 1.

Each heating element comprises a regulating member which may be of any conventional type and has not been shown.

The heating means 4 is adapted to maintain the lower part 2 of tube 1 at a temperature preferably of constant value, lower than 400° C. and more particularly from 200° to 400° C.

The heating means 5 is adapted to maintain the upper part 3 of tube 1 preferably at a constant temperature higher than 400° C., in the range from 400° C. to 700° C. and more particularly from 550° C. to 600° C.

The upper part 10 of tube 1 is maintained at the same temperature as portion 3 of tube 1, which communicates through a duct 10a of small diameter with a device 11 for detecting and measuring the amount of hydrocarbon compounds discharged from tube 1.

The device for selectively detecting the hydrocarbon compounds will for example comprise a flame ionization detector of conventional use in gas chromatography.

The detector 11 delivers a signal S representative of the measured amounts of hydrocarbon compounds. This signal may be transmitted to a recording device 12, so as to be displayed, if desired.

The apparatus according to the invention also comprises a cup 7 wherein is placed the sample to be analyzed. This cup may be displaced, so as to be introduced into the tube, by any suitable means, such as, for example, a piston 6 associated with automatic or manual displacement means 6a which may be constituted by a cylinder forming with piston 6 a double-acting jack connected to a source of fluid or, alternately, by a toothed wheel or pinion, which can be rotated and cooperates with a rack integral with piston 6.

The piston 6 will preferably be hollow. It is connected at its lower end with pipe 8 delivering a carrier gas which may be a non-oxydizing gas, such as an inert gas (nitrogen, helium . . . ), or hydrogen.

Means 9 provides for insulation and sealing around piston 6. Such means may optionally be displaceable to facilitate the introduction of the sample into cup 7.

The operation of the apparatus is as follows:

The sample to be analyzed is introduced into cup 7. This sample preferably of small size, with a weight not exceeding 100 mg can be analyzed without preliminary treatment, even if it comes from drill cuttings. Alternatively the sample may be subjected to some preliminary treatments such as moderate drying, grinding, etc.

The apparatus is then in the position illustrated by FIG. 1. The heating means 4 and 5 are energized and when parts 2 and 3 have both reached the desired temperatures the cup 7 is introduced at time $t_o$ into tube 1, first in the lower part thereof (FIG. 1A).

Under the action of the temperature which is set at a value in the range from 200° C. to 400° C., the whole amount of the native hydrocarbons contained in the sample is vaporized and then detected and measured by device 11.

At time $t_1$, when substantially all the hydrocarbons have been vaporized, piston 6 is rapidly moved upwardly (FIG. 1) and the cup 7 is positioned in part 3 of tube 1 (FIG. 1B). The rate of this displacement is such that the sample is subjected to a temperature variation of at least 20° C. per minute. Under the influence of the high temperature (preferably from 550° C. to 600° C.) the whole organic material contained in the sample is pyrolyzed. When, at time $t_2$, the whole amount of these hydrocarbon compounds produced by the pyrolysis has been detected and measured by device 11, piston 6 may be retracted to its initial position (FIG. 1).

FIG. 2 shows versus time t the general shape of signal "S" delivered by device 11 between the instants $t_o$ and $t_2$. As apparent from this drawing, this signal generally comprises two separate peaks $P_1$ and $P_2$. The first peak, of amplitude $H_1$, appears during the time interval $[t_o-t_1]$ and corresponds to the native hydrocarbons originally present in the sample. The second peak, of amplitude $H_2$, appears during the time interval $[t_1-t_2]$ and corresponds to the hydrocarbon compounds produced by pyrolysis of the organic material of the sample. When piston 6 is displaced through automatic means 6a, such means may be energized by signal S.

For example, when at time $t_1$, this signal has reached, while decreasing, a lower limit, the means 6a moves the piston 6 upwardly (FIG. 1), so as bring the cup 7 into part 3 of tube 1.

From the values $H_1$ and $H_2$ of peaks $P_1$ and $P_2$ it is possible to characterize the rock as folllows:

(1) high values of $H_2$ depict a source rock of good quality, containing the more hydrocarbons as, simultaneously, the value of $H_1$ is greater, (2) moderate or average values of $H_2$ depict a mother rock of average quality, containing the more hydrocarbons as simultaneously the value of $H_1$ is grater, greater, (3) small values of $H_2$ depict either
  (a) a rock of no interest for hydrocarbon production, if simultaneously the value of $H_1$ is small,
  (b) some indication of hydrocarbons when simultaneously the value of $H_1$ is moderate,
  (c) a reservoir rock filled with hydrocarbons when simultaneously the value of $H_1$ is high.

It will be obviously also possible, without departing from the scope of the present invention, to consider the integrated values of signals $P_1$ and $P_2$, instead of their maximum or peak values $H_1$ and $H_2$.

FIG. 3 shows, by way of example, a particular embodiment of the method according to the invention, carried out during a drilling operation.

The above defined measurements are performed on samples of cuttings contained in the drill mud. For each analyzed sample, the device 12 records on two separate graphs the values of $H_1$ and $H_2$ versus depth P from which the sample originates, this depth being measured by any known device 12a which will not be described here and which, in association with the apparatus of FIG. 1, delivers to the recording means 12 a signal representative of the depth from which the sample originates.

A double graph as illustrated by FIG. 3 is thus obtained, whereon in the above-indicated manner, it is easy to locate with accuracy:

geological formations of no interest for hydrocarbon production (zones I, III, VII, IX), geological formations formed of source rocks of moderate or average quality (zone II), geological formations formed of good source rocks wherein hydrocarbon are contained (zone IV) or partially contained (zone V), geological formations constituting reservoir zones containing hydrocarbons (zone VI), and geological formations with only oil shows (zone VIII)

All the so-obtained data enable the field geologist to get an accurate knowledge of oil-related characteristics of the traversed geological formations.

FIG. 4 diagrammatically shows an apparatus modified for carrying out the first embodiment of the method according to the invention.

In addition to the above-described devices, this apparatus comprises a circuit 13 for processing the signals recorded in device 12.

Circuit 13 delivers a signal S representing the ratio $H_1/H_2$, this signal being transmitted to and recorded in the device 14 which receives simultaneously a second signal representing a selected second parameter.

In the embodiment of FIG. 4, this second parameter is the amplitude $H_2$ of peak $P_2$ (FIG. 2) which is directly transmitted from device 12 to device 14.

The pair of values $H_1/H_2$ and $H_2$ makes it possible to determine as follows, the oil-related characteristics:

high and moderate values of $H_2$ characterize source rocks of respectively good and average quality, these source rocks containing more hydrocarbons as the value of the ratio $H_1/H_2$ is higher, low values of $H_2$ depict rocks of no interest for hydrocarbon production, if simultaneously the value of the ratio $H_1/H_2$ is small, oil shows if simultaneously the value of the ratio $H_1/H_2$ is moderate, reservoir-rocks filled with hydrocarbons if simultaneously the value of the ratio $H_1/H_2$ is high.

It will be obviously possible to characterize the studied rocks by examining the couple of values $H_1/H_2$ and $H_1$.

Like the above embodiment, this other embodiment of the method according to the invention may advantageously be carried out on the drill field as drilling proceeds, the device 12a for measuring the depth of the drilled well being then connected to the recording device 14, as indicated in dotted line in FIG. 4.

It has also been discovered that, for a given drilled hole, the ratio $H_1/H_2$ increases regularly with the burying depth (FIG. 5), irrespective of the type of organic material contained in the studied samples, as long as these samples are not affected by migration phenomena.

In this case the values taken by ratio $H_1/H_2$ provides a delimitation of the oil- and gas-bearing zones around the wellbore: gas-bearing formations are characterized by values of $H_1/H_2$ greater than 0.5, while oil-bearing zones are characterized by values of $H_1/H_2$ lower than 0.5.

The phenomena of oil migration are made apparent by abnormal value of $H_1/H_2$, as compared to the values of the average curve of FIG. 5, in particular:

values of $H_1/H_2$ substantially higher than those of the average curve (level A in FIG. 5) depict oil impregnated reservoirs (these reservoir levels are also recognizable by their low value of parameter $H_2$);

values of $H_1/H_2$ slightly in excess (level B of FIG. 5) correspond to small oil accumulations (or oil shows);

on the contrary, values of $H_1/H_2$ lower than that of the average curve (level C of FIG. 5) characterize geological levels which have lost hydrocarbons through drainage (these levels generally corresponding to mother rocks whch have also a high value of $H_2$).

FIG. 6 diagrammatically shows a first simplified embodiment of the apparatus according to the invention illustrated by FIG. 1, or the alternative embodiment shown in FIG. 4. Same references have been used in FIG. 6 to designate same parts of the apparatus. In this embodiment a single element 5 has been used to heat the upper part of tube 1 to a temperature capable of pyrolyzing the insoluble organic material of the analyzed sample. This temperature, higher than 400° C., will generally be from 400° C. to 700° C., and more particularly from 550° C. to 600° C., and may or not be kept substantially constant. Furthermore, means (not shown) makes it possible to delimit at the lower part 2 of tube 1 a zone wherein the temperature is lower than 400° C. and preferably from 200°C. to 400° C.

Ths apparatus is operated as follows:

The sample to be analyzed is introduced into cup 7. The apparatus is then in the position shown in solid line in FIG. 6. The heating means 5 is energized so as to create in the upper part of tube 1 the desired temperature, in the range from 400° to 700° C. Though a (not illustrated) detection means, such as a thermometer, a zone at a temperature in the range from 200° C. to 400° C. is delimited in the lower part of tube 1.

At instant $t_o$ the cup 7 is moved so as to be very accurately positioned in said zone (position of cup 7 shown in dashed line). At time $t_1$, when all native hydrocarbons, originally present in the sample, have been volatilized, cup 7 is again displaced so as to be introduced into the upper part of tube 3 wherein, under the influence of the high temperature, all the organic material of the sample is pyrolyzed (position of cup 7 shown in dotted line).

When at time $t_2$ the whole amount of hydrocarbon compounds resulting from this pyrolysis has been detected and measured by device 11, piston 6 may be retracted to its initial position.

The zone at the lower part of tube 1 wherein prevails a temperature sufficient for vaporizing the hydrocarbons contained in the sample without however pyrolyzing the organic material contained in the sample may be delimited before analyzing each sample, but it is also possible to determine this zone during preliminary tests corresponding to a calibration of the apparatus.

FIG. 7 represents another embodiment of the apparatus having the advantage of a greater compactness and which reduces to a minimum the displacements of cup 7. This embodiment comprises only one element 5 which heats the whole tube 1, this tube being of as short as permitted by the length of cup 7. A control means 5a whose utility will become apparent hereinunder permits an automatic or manual control of the operation of the heating means 5.

The apparatus of FIG. 7 operates as follows:

The sample to be analyzed is introduced into cup 7 which is in the position shown in solid line in FIG. 7. The heating means 5 is energized and its operation controlled by control means 5a, so that the temperature inside the tube 1 lower than 400° C., and preferably ranges from 200° to 400° C. At the time $t_o$ the cup 7 is introduced into tube 1 (position shown in dotted line in FIG. 7).

At time $t_1$, when all the hydrocarbons contained in the sample have been vaporized, control means 5a is actuated so as to modify the operation of the heating means 5 which raises (preferably at a very rapid rate)

the temperature within tube 1 up to a temperature in the range from 400° C. to 700° C., and more particularly from 550° C. to 600° C.

More precisely, the control means 5a modifies the operation of the heating means 5 so that the temperature variation, after vaporizing the native hydrocarbons without however pyrolyzing the insoluble organic material, is at least 20° C. per minute. At time $t_2$ all the organic material contained in the sample has been pyrolyzed and control means 5a adjusts the operation of heating means 5, so that the temperature in tube 1 is lowered back to a value at most equal to 400° C., in order to carry out the analysis of a new sample.

In this embodiment the apparatus is so designed that tube 1 has a very low thermal inertia.

We claim:

1. A method for rapidly evaluating at least one oil-related characteristic of a geological sediment containing native hydrocarbons and insoluble organic materials using small-sized samples thereof, comprising:
    (a) heating the sample to a first temperature for vaporizing substantially all the native hydrocarbons contained in the sample, without pyrolyzing the insoluble organic material of this sample,
    (b) determining a first parameter representing the amount of these native hydrocarbons,
    (c) heating the sample to a second temperature to pyrolyze substantially all the insoluble organic material contained in the sample
    (d) determining a second parameter representing the amount of hydrocarbon products resulting from the pyrolysis of the insoluble organic material of the sample, and
    (e) deducing from said two determinations at least one oil-related characteristic of the geological sediment.

2. A method according to claim 1, wherein said first temperature is at most 400° C.

3. A method according to claim 2, wherein said first temperature is in the range from 200° C. to 400° C.

4. A method according to claim 1, wherein the value of said first temperature is maintained substantially constant during the step (a) of the method.

5. A method according to claim 1, wherein said second temperature is higher than 400° C.

6. A method according to claim 5, wherein said second temperature is in the range from 550° C. to 600° C.

7. A method according to claim 1, wherein the value of said second temperature is kept substantially constant during step (c) of the method.

8. A method according to claim 1, wherein after determination of said first parameter, the temperature is raised from said first value to said second value at a rate of at least 20° C. per minute.

9. A method according to claim 1, comprising the determination of a third parameter proportional to the ratio of said first parameter to said second parameter, and wherein at least one oil-related characteristic of the geological sediment is derived from said third parameter and from at least one of said first and second parameters.

10. A method according to claim 1 which enables locating among the geological formations traversed by a borehole those having oil characteristics substantially different from the oil characteristics of the other formations, this method comprising determining a third parameter representing the ratio of said first and second parameters for samples originating from different depths, determinig the curve of the average variation of said third parameter versus depth, and locating said formations having said different characteristics by determining the formations for which the value of said third parameter substantially differs from the value given by said average curve.

* * * * *